(12) United States Patent
Balasubramanian et al.

(10) Patent No.: US 9,198,770 B2
(45) Date of Patent: Dec. 1, 2015

(54) ARTIFICIAL DISC DEVICES AND RELATED METHODS OF USE

(71) Applicant: GLOBUS MEDICAL, Inc., Audubon, PA (US)

(72) Inventors: Anand Balasubramanian, Collegeville, PA (US); Jeffrey Bennet Bennett, Pottstown, PA (US); Noah Hansell, King of Prussia, PA (US)

(73) Assignee: Globus Medical, Inc., Audubon, PA (US)

( * ) Notice: Subject to any disclaimer, the term of this patent is extended or adjusted under 35 U.S.C. 154(b) by 172 days.

(21) Appl. No.: 13/955,477

(22) Filed: Jul. 31, 2013

(65) Prior Publication Data

US 2015/0039089 A1 Feb. 5, 2015

(51) Int. Cl.
*A61F 2/44* (2006.01)
*A61F 2/30* (2006.01)

(52) U.S. Cl.
CPC .............. *A61F 2/442* (2013.01); *A61F 2/4425* (2013.01); *A61F 2/30767* (2013.01); *A61F 2002/30364* (2013.01); *A61F 2002/30365* (2013.01); *A61F 2002/30387* (2013.01); *A61F 2002/30462* (2013.01); *A61F 2002/30563* (2013.01); *A61F 2002/30578* (2013.01); *A61F 2002/30884* (2013.01); *A61F 2002/30932* (2013.01); *A61F 2002/443* (2013.01); *A61F 2002/4435* (2013.01)

(58) Field of Classification Search
CPC ............ A61F 2/442; A61F 2220/0025; A61F 2002/30563; A61F 2/4425; A61F 2310/00023; A61F 2002/30604; A61F 2250/0018; A61F 2002/30014

USPC ................... 623/17.11–17.16; 606/246–249
See application file for complete search history.

(56) References Cited

U.S. PATENT DOCUMENTS

| | | |
|---|---|---|
| 3,867,728 A | 2/1975 | Stubstad |
| 4,759,766 A | 7/1988 | Buettner-Janz |
| 4,997,432 A | 3/1991 | Keller |
| 5,122,130 A | 6/1992 | Keller |
| 5,246,458 A | 9/1993 | Graham |
| 5,258,031 A | 11/1993 | Salib |
| 5,314,477 A | 5/1994 | Marnay |
| 5,401,269 A | 3/1995 | Buttner-Janz |
| 5,425,773 A | 6/1995 | Boyd |
| 5,458,031 A | 10/1995 | Wolff |
| 5,507,816 A | 4/1996 | Bullivant |
| 5,534,029 A | 7/1996 | Shima |
| 5,556,431 A | 9/1996 | Buettner-Janz |
| 5,562,738 A | 10/1996 | Boyd |

(Continued)

FOREIGN PATENT DOCUMENTS

| | | |
|---|---|---|
| EP | 0955021 B1 | 3/1998 |
| WO | 99/05995 A1 | 2/1999 |

(Continued)

*Primary Examiner* — Mary Hoffman
*Assistant Examiner* — Tara R Carter

(57) ABSTRACT

An artificial disc is disclosed. The artificial disc may include a superior endplate having a bi-convex superior surface and a concave inferior surface, and an inferior endplate having a bi-convex inferior surface. The artificial disc may also include a core assembly disposed between the superior endplate and the inferior endplate, and a support assembly disposed on outer surfaces of both the superior endplate and the inferior endplate. The support assembly may be configured to couple the superior endplate to the inferior endplate.

5 Claims, 8 Drawing Sheets

(56) References Cited

U.S. PATENT DOCUMENTS

| | | |
|---|---|---|
| 5,676,701 A | 10/1997 | Yuan |
| 5,683,465 A | 11/1997 | Shinn |
| 5,755,796 A | 5/1998 | Ibo |
| 5,776,202 A | 7/1998 | Copf |
| 5,888,226 A | 3/1999 | Rogozinski |
| 5,895,428 A | 4/1999 | Berry |
| 5,899,941 A | 5/1999 | Nishijima |
| 6,019,792 A | 2/2000 | Cauthen |
| 6,039,763 A | 3/2000 | Shelokov |
| 6,063,121 A | 5/2000 | Xavier |
| 6,080,157 A | 6/2000 | Cathro |
| 6,113,637 A | 9/2000 | Gill |
| 6,146,421 A | 11/2000 | Gordon |
| 6,146,422 A | 11/2000 | Lawson |
| 6,156,067 A | 12/2000 | Bryan |
| 6,228,118 B1 | 5/2001 | Gordon |
| 6,368,350 B1 | 4/2002 | Erickson |
| 6,375,682 B1 | 4/2002 | Fleischmann |
| 6,416,551 B1 | 7/2002 | Keller |
| 6,468,310 B1 | 10/2002 | Ralph |
| 6,540,785 B1 | 4/2003 | Gill |
| 6,635,087 B2 | 10/2003 | Angelucci |
| 6,660,007 B2 | 12/2003 | Khanna |
| 6,682,562 B2 | 1/2004 | Viart |
| 6,706,068 B2 | 3/2004 | Ferree |
| 6,712,852 B1 | 3/2004 | Chung |
| 6,936,071 B1 | 8/2005 | Marnay |
| 6,986,789 B2 | 1/2006 | Schultz |
| 6,997,953 B2 | 2/2006 | Chung |
| 7,198,644 B2 | 4/2007 | Schultz |
| 7,582,115 B2 | 9/2009 | Weber |
| 7,585,325 B2 | 9/2009 | Schneid |
| 7,641,666 B2 | 1/2010 | Paul |
| 7,704,280 B2 | 4/2010 | Lechmann |
| 7,708,777 B2 | 5/2010 | O'Neil |
| 7,713,304 B2 | 5/2010 | Ankney |
| 7,811,329 B2 | 10/2010 | Ankney |
| 7,867,279 B2 | 1/2011 | Hester |
| 7,892,262 B2 | 2/2011 | Rhoda |
| 7,909,876 B2 | 3/2011 | Dooris |
| 7,909,877 B2 | 3/2011 | Krueger |
| 7,927,373 B2 | 4/2011 | Parsons |
| 8,133,281 B2 | 3/2012 | Lechmann |
| 2002/0035400 A1 | 3/2002 | Bryan |
| 2002/0111681 A1 | 8/2002 | Ralph |
| 2002/0111682 A1 | 8/2002 | Ralph |
| 2002/0111683 A1 | 8/2002 | Ralph |
| 2002/0111684 A1 | 8/2002 | Ralph |
| 2002/0111685 A1 | 8/2002 | Ralph |
| 2002/0111686 A1 | 8/2002 | Ralph |
| 2002/0111687 A1 | 8/2002 | Ralph |
| 2002/0120335 A1 | 8/2002 | Angelucci |
| 2003/0045935 A1 | 3/2003 | Angelucci |
| 2003/0045936 A1 | 3/2003 | Angelucci |
| 2003/0069643 A1* | 4/2003 | Ralph et al. ................. 623/17.13 |
| 2003/0125738 A1 | 7/2003 | Khanna |
| 2003/0125740 A1 | 7/2003 | Khanna |
| 2003/0204261 A1 | 10/2003 | Eisermann |
| 2003/0208273 A1 | 11/2003 | Eisermann |
| 2003/0233094 A1 | 12/2003 | Squires |
| 2004/0030388 A1 | 2/2004 | Null |
| 2004/0064184 A1 | 4/2004 | Chung |
| 2004/0117021 A1 | 6/2004 | Biedermann et al. |
| 2004/0117022 A1 | 6/2004 | Marnay |
| 2004/0133278 A1 | 7/2004 | Marino |
| 2004/0138750 A1 | 7/2004 | Mitchell |
| 2004/0143332 A1 | 7/2004 | Krueger |
| 2004/0153155 A1 | 8/2004 | Chung |
| 2004/0153157 A1 | 8/2004 | Keller |
| 2004/0172135 A1 | 9/2004 | Mitchell |
| 2004/0210222 A1 | 10/2004 | Angelucci |
| 2004/0215198 A1 | 10/2004 | Marnay |
| 2004/0220582 A1 | 11/2004 | Keller |
| 2004/0225365 A1 | 11/2004 | Eisermann |
| 2004/0243240 A1 | 12/2004 | Beaurain |
| 2005/0021145 A1 | 1/2005 | de Villiers |
| 2005/0033438 A1 | 2/2005 | Schultz |
| 2005/0038511 A1 | 2/2005 | Martz |
| 2005/0043800 A1 | 2/2005 | Paul |
| 2005/0043803 A1 | 2/2005 | Schultz |
| 2005/0045936 A1 | 3/2005 | Chang |
| 2005/0085917 A1 | 4/2005 | Marnay |
| 2005/0107877 A1 | 5/2005 | Blain |
| 2005/0131412 A1 | 6/2005 | Olevsky |
| 2005/0149189 A1 | 7/2005 | Moktar |
| 2005/0251138 A1 | 11/2005 | Boris |
| 2005/0251261 A1 | 11/2005 | Peterman |
| 2005/0261773 A1 | 11/2005 | Ferree |
| 2005/0267581 A1 | 12/2005 | Marnay |
| 2005/0273100 A1 | 12/2005 | Taylor |
| 2006/0020341 A1 | 1/2006 | Schneid |
| 2006/0069437 A1 | 3/2006 | Weber |
| 2006/0116768 A1 | 6/2006 | Krueger |
| 2006/0178746 A1* | 8/2006 | Bartish et al. ............... 623/17.13 |
| 2006/0229724 A1 | 10/2006 | Lechmann |
| 2006/0229725 A1 | 10/2006 | Lechmann |
| 2006/0293752 A1* | 12/2006 | Moumene et al. ......... 623/17.13 |
| 2007/0010826 A1 | 1/2007 | Rhoda |
| 2007/0021837 A1 | 1/2007 | Ashman |
| 2007/0055378 A1* | 3/2007 | Ankney et al. ............. 623/17.15 |
| 2007/0100454 A1 | 5/2007 | Burgess |
| 2007/0173936 A1 | 7/2007 | Hester |
| 2007/0191952 A1 | 8/2007 | Bernero |
| 2007/0260317 A1 | 11/2007 | Ankney |
| 2007/0265707 A1 | 11/2007 | Marnay |
| 2008/0051901 A1 | 2/2008 | de Villiers |
| 2008/0161930 A1 | 7/2008 | Carls |
| 2009/0005872 A1* | 1/2009 | Moumene et al. ......... 623/17.16 |
| 2009/0012619 A1 | 1/2009 | Cordaro |
| 2009/0043391 A1 | 2/2009 | de Villiers |
| 2009/0054986 A1 | 2/2009 | Cordaro |
| 2009/0062920 A1 | 3/2009 | Tauber |
| 2009/0088853 A1* | 4/2009 | Ogilvie et al. ............. 623/17.16 |
| 2009/0192617 A1 | 7/2009 | Arramon et al. |
| 2010/0016972 A1 | 1/2010 | Jansen |
| 2010/0042220 A1 | 2/2010 | Tauber |
| 2010/0280617 A1 | 11/2010 | Coppes |
| 2010/0286784 A1 | 11/2010 | Curran |
| 2011/0035010 A1 | 2/2011 | Harrington |
| 2011/0054618 A1 | 3/2011 | Lechmann |
| 2011/0087331 A1 | 4/2011 | Reichen |
| 2011/0098819 A1 | 4/2011 | Eisermann |
| 2011/0106263 A1 | 5/2011 | Eisermann |
| 2011/0160772 A1* | 6/2011 | Arcenio et al. ............... 606/248 |
| 2011/0172773 A1 | 7/2011 | Reichen |
| 2011/0257747 A1 | 10/2011 | Copf |
| 2013/0110240 A1 | 5/2013 | Hansell et al. |
| 2013/0184766 A1 | 7/2013 | Black |

FOREIGN PATENT DOCUMENTS

| | | |
|---|---|---|
| WO | 00/23015 A1 | 4/2000 |
| WO | 00/42944 A1 | 7/2000 |
| WO | 2007/023399 A1 | 3/2007 |

* cited by examiner

ARTIFICIAL DISC DEVICES AND RELATED METHODS OF USE

TECHNICAL FIELD

Various embodiments of the present disclosure relate generally to artificial disc devices and related systems and methods. More specifically, the present disclosure relates to devices, systems, and methods for repairing and/or replacing intervertebral discs of a patient.

BACKGROUND

The spine is composed of several individual bones, known as vertebrae. The vertebrae vary in size, shape, and function in different regions of the spine. The cervical vertebrae make up the bones of the neck and provide for much of the movement of the head. The thoracic vertebrae act as anchors for the ribs and are relatively immobile. The lumbar vertebrae, located at the base of the spine, are the largest vertebrae and allow movement and articulation of the trunk.

In between adjacent vertebrae is an intervertebral disc, which consists of a fibrous outer portion and a gelatinous inner portion. The discs allow the vertebrae to move and articulate relative to one another. They also act as a shock absorber when there is a blow to the spine, such as from a fall or a strike on the head. In particular, an intervertebral disc is capable of at least six different motions or degrees of freedom: flexion, which is bending forward from the waist; extension, which is bending backward from the waist; lateral bending, or leaning sideways; axial rotation, which is turning or twisting to one side or the other; axial deflection, which may also be known as axial compression, vertical extension, or compression along the spine; and anterior/posterior (A/P) translation, which is when one vertebrae slides forward or backward relative to an adjacent vertebra without changing its angle relative to the neighboring vertebra.

The intervertebral disc can be injured or damaged as a result of aging, trauma, or disease. The disc can become desiccated or otherwise loosen or weaken in structure, a condition known as degenerative disc disorder (DDD). A herniated disc is one that has developed a tear in the outer portion, allowing the inner portion (e.g., the internal gelatinous portion) to push out. In any case, a damaged disc no longer permits movement as it once did, which may cause pain and/or discomfort to a patient. For example, as the vertebrae move out of their normal, healthy position, the patient may develop chronic, and in some case debilitating, pain as nerves are compressed.

Historically, the injured disc, in a condition such as DDD or herniated disc, can be treated with spinal fusion. Spinal fusion can also be indicated as a treatment for tumors, fractures, and conditions such as scoliosis and kyphosis. In the fusion procedure, a discectomy is performed to remove the damaged disc and the adjacent vertebrae are physically joined together with rods, wire, or other instrumentation. A bone graft may be placed between the vertebrae, and over several months, the vertebrae grow together. A typical fusion patient does not notice any loss in mobility because her range of motion was even more restricted by the original condition or injury.

Nevertheless, the lack of motion between the fused vertebrae places increased stress on the surrounding vertebrae and intervertebral discs. This increased stress may lead to premature failure or injury to these components, requiring further treatment. In addition, a fusion procedure may be a major operation, requiring open back surgery and a long recovery period. For these reasons, it is typically a treatment of last resort, reserved for severe cases or when other treatment options have failed.

Alternatives to the open spine fusion procedure, including minimally invasive procedures and artificial disc replacements, are in various stages of development and practice, but these alternatives have yet to see widespread adoption. Minimally invasive procedures involve the use of small incisions, remote control manipulation of instruments, and observation through an endoscope or similar access device. These procedures may result in less trauma to the patient and improved recovery times. Minimally invasive surgery can also be used to replace an injured intervertebral disc. Instead of fusing the vertebrae above and below a damaged or diseased disc, the disc can be replaced with an artificial or prosthetic disc, for example. Current prosthetic discs may provide a greater range of motion than an equivalent fusion procedure while offering equal or better treatment of the condition.

Current artificial discs, however, may have a plurality of interlocked components that may be subject to inadvertent separation after surgical procedures. Such disassembly may require additional procedures to correct. Accordingly, there is a need for an artificial disc that enables all six degrees of movement, restricts movement along one or more degrees, is compatible with a non-anterior surgical procedure, and has increased durability.

SUMMARY OF THE DISCLOSURE

The present disclosure relates to embodiments of artificial discs and related methods of use.

In accordance with an embodiment, an artificial disc may include a superior endplate having a bi-convex superior surface and a concave inferior surface, and an inferior endplate having a bi-convex inferior surface. The artificial disc also may include a core assembly disposed between the superior endplate and the inferior endplate, and a support assembly disposed on outer surfaces of both the superior endplate and the inferior endplate. The support assembly may be configured to couple the superior endplate to the inferior endplate.

Various embodiments of the disclosure may include one or more of the following aspects: wherein the core assembly may include a superior core comprising a convex superior surface configured to contact the concave inferior surface of the superior endplate, and a flexible inferior core configured to connect to the superior core and the inferior endplate; wherein the support assembly may include a first groove disposed in an outer surface of the superior endplate, and a second groove disposed in an outer surface of the inferior endplate; wherein the support assembly may further include a sheath disposed within the first and second grooves; may further include at least one aperture disposed in the first groove, at least one aperture disposed in the second groove, and a plurality of fasteners disposed through the sheath and the at least one aperture of both the first and second grooves; may further comprise a first serrated keel located on the superior surface of the superior endplate, and a second serrated keel located on the inferior surface of the inferior endplate; wherein at least one of the superior and inferior endplates may be configured to promote bony on-growth; may further include a protrusion extending from at least one of the biconvex surface of the superior endplate or the inferior endplate, the protrusion being partially spherical, partially barrel-shaped, or partially cylindrical; wherein the superior endplate, the core assembly, and the inferior endplate may be stacked along a first axis, and the first serrated keel or second serrated keel may extend further outward along the first axis than the protrusion.

In accordance with an embodiment, an artificial disc assembly may include an artificial disc. The artificial disc may include a superior endplate having a bi-convex superior surface and a concave inferior surface, and an inferior endplate having a bi-convex inferior surface. The artificial disc may also include a core assembly secured to the superior endplate and the inferior endplate. The superior endplate and inferior endplate may articulate with respect to each other only by the elasticity of the core assembly.

Various embodiments of the disclosure may include one or more of the following aspects: wherein exterior surfaces of the artificial disc may be configured such that when the artificial disc is installed between vertebral bodies, the exterior surfaces do not encourage bony on-growth; may further include a cover plate configured to retain the artificial disc between a pair of vertebral bodies; wherein the cover plate may be formed from a shape memory material; wherein the core assembly may include at least one securing mechanism extending from an outer surface, the securing mechanism may be formed from the same material as the core assembly, configured to compress radially inward from a rest position when a compressive force is applied, and move toward the rest position when the compressive force is removed; may further include a protrusion extending from at least one of the biconvex surface of the superior endplate or the inferior endplate, the protrusion being partially spherical, partially barrel-shaped, or partially cylindrical.

In accordance with a further embodiment, a method of installing an artificial disc within a patient may include the artificial disc with a superior endplate having a bi-convex superior surface, and a concave inferior surface. The artificial disc may also include an inferior endplate having a bi-convex inferior surface, and a core assembly secured to the superior endplate and the inferior endplate. The superior endplate and inferior endplate may articulate with respect to each other only by the elasticity of the core assembly. The method may include forming an opening in a vertebral disc annulus, and removing damaged vertebral disc material through the opening. The method may also include inserting the artificial disc between through the opening between a pair of adjacent vertebral bodies, and securing the artificial disc between the vertebral bodies.

Various embodiments of the disclosure may include one or more of the following aspects: wherein securing the artificial disc between the vertebral bodies may include securing a cover plate to at least one of the vertebral disc annulus and the inner circumference of one of the vertebral bodies to cover the opening; wherein securing the artificial disc between the vertebral bodies may further include suturing the cover plate to at least one of the vertebral disc annulus and at least one of the pair of vertebral bodies; wherein the core assembly may include at least one securing mechanism extending from an outer surface, inserting the artificial disc may further include applying a compressive force to the securing mechanism, and securing the artificial disc between the vertebral bodies may include releasing the compressive force applied to the securing mechanism to allow the securing mechanism to secure against at least one of the vertebral disc annulus and the inner circumference of one of the vertebral bodies; and wherein securing the artificial disc between the vertebral bodies may further include suturing the securing mechanism to at least one of the vertebral disc annulus and at least one of the pair of vertebral bodies.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Figure 1:
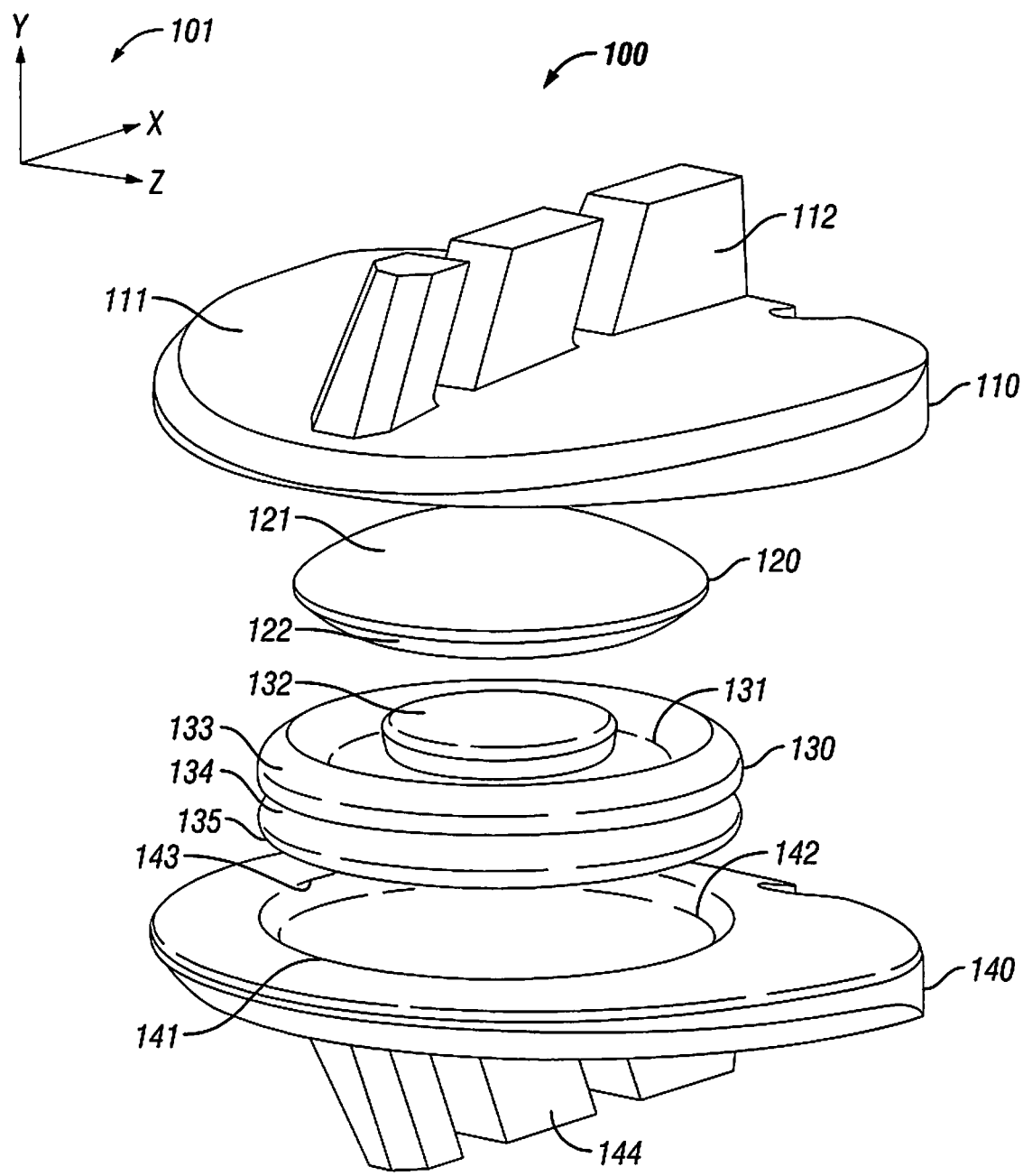
FIG. 1 is an exploded view illustration of an artificial disc in accordance with an embodiment of the present disclosure.

According to an aspect of the disclosure, an artificial disc 100 may be capable of providing all six of the six degrees of movement afforded by native intervertebral discs. An example of this type of artificial disc is shown in an exploded view in FIG. 1. Artificial disc 100 may include a superior endplate 110, a superior core 120, an inferior core 130, and an inferior endplate 140. Superior endplate 110 and inferior endplate 140 may be formed from a rigid, bio-compatible material such as, e.g., titanium or polyetheretherketone (PEEK), among others. Components that contact bone, including superior endplate 110 and inferior endplate 140, may be treated with a titanium and/or hydroxyapatite plasma spray coating to encourage bony on-growth, improving the strength and stability of the connection between the respective component and the underlying bone (e.g., a vertebral body). Any other suitable coating may also be provided on either superior endplate 110 or inferior endplate 140. Such coatings may include therapeutic agents, if desired. Superior endplate 100 and/or inferior endplate 140 may also include radiopaque markings to facilitate in vivo visualization. Inferior core 130 may be formed from a polymer, such as, e.g., polycarbonate urethane (PCU) or another suitable polymer, that may allow disc 100 to be compressed along its vertical axis.

Axes 101 may represent the three-dimensional orientation of the artificial disc 100. For example, the X axis may be approximately aligned with or parallel to an anterior/posterior axis of disc 100. The Y axis may be substantially parallel to a superior/inferior axis of disc 100. The Y axis may also be somewhat indicative of a vertical axis of the spine, which may be commonly referred to simply as the axis of the spine. The Z axis may be approximately parallel to a lateral axis of disc 100.

Superior endplate 110 may have an upper or superior surface 111. Superior endplate 110 may have a variable cross-section. Superior surface 111 may be bi-convex, i.e., curved from left to right and front to back, or may have another suitable configuration. This curvature may give surface 111 a partial dome or spherical shape. The curvature may be complementary to the natural curvature of an endplate of an adjacent vertebral body and may provide for an anatomical fit between surface 111 and the vertebral body (not shown in FIG. 1). One or more serrated keels 112 may be located on superior surface 111 and may extend at an angle from superior surface 111. Each keel 112 may have a longitudinal axis that is roughly aligned along an anterior/posterior axis of disc 100. Once a discectomy has been completed, removing the damaged natural disc or damaged disc material, a groove or channel may be cut into the vertebral body (not shown) to receive each keel 112. Each keel 112 may be integrally formed with superior surface 111 or may alternatively be attached to superior surface 111 by a suitable securing mechanism, e.g., an adhesive. Each keel 112 may have one more holes, e.g., through holes, or openings (not shown) perpendicular to the longitudinal axis of the keel. These holes or openings may provide an aperture for bony in-growth, which may strengthen the connection or interface between the endplate and the vertebral body. In some embodiments, superior surface 111 may include three keels 112, although any other number of keels 112 may alternatively be utilized. Each of the plurality of keels 112 may have the same dimensions as the remaining plurality of keels 112. Alternatively a given keel 112 may have different dimensions than other keels 112. All of the plurality of keels 112 may extend along a common axis, although other configurations may alternatively be utilized, such as, e.g., non collinear spacing of keels on superior surface 111. In some embodiments, keels 112 may be arranged in a plurality of rows and/or columns, if desired. Keels 112 may include suitable coatings or other geometrical features (e.g., barbs or other protrusions) to promote bony in-growth/on-growth. Keels 112 may have varying lengths, widths, and/or other dimensions.

Figure 2:
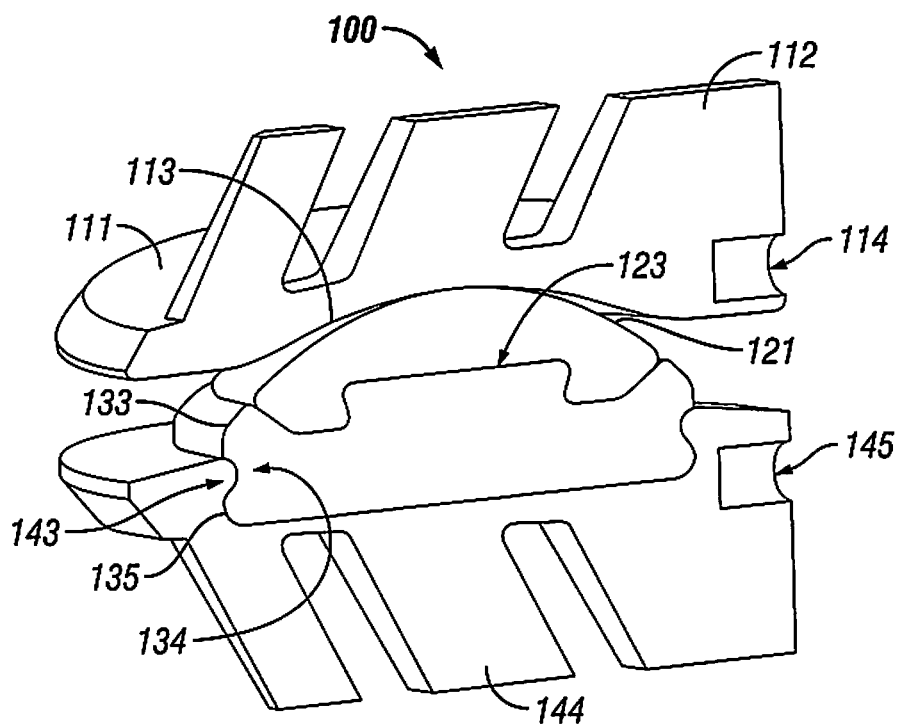
FIG. 2 is a cross-sectional view illustration of an artificial disc in accordance with an embodiment of the present disclosure.

Superior core 120 may have a superior mating surface 121 that is domed or curved. Surface 121 may be configured to contact a concave inferior surface 113 (shown only in FIG. 2) of superior endplate 110. Superior core 120 may also have an inferior surface 122 that mates with a corresponding portion of inferior core 130. Superior core 120 may be made from a hard material suitable for bearing contact, such as, for example, titanium, cobalt-chromium-molybdenum (Co—Cr—Mo) alloy, ceramic, PEEK, or the like. Superior core 112 may include a suitable coating to facilitate relative movement, such as, e.g., a lubricous coating.

Inferior core 130 may be generally cylindrical in shape, although other shapes are also contemplated. Superior surface 131 of inferior core 130 may be substantially concave with a mating knob 132 for attaching to a corresponding feature of cavity (not shown) of superior core 120. Inferior core 130 may be divided into an upper side 133 and a lower side 135 by a mating groove 134. Mating groove 134 may help to attach inferior core 130 to inferior endplate 140.

Inferior endplate 140 may have a mating socket 142 formed in its superior surface 141. Mating socket 142 may include a mating rim 143 that is complementary to mating groove 134 of the inferior core 130. Mating socket 142 may have an overall shape that is complementary to the lower portion of inferior core 130. Inferior core 130 may fit into and be retained by mating socket 142. Inferior endplate 140 may additionally have one or more serrated keels 144 that may be substantially similar to keels 112 in shape, structure, design, and/or configuration. A given keel 144 may have a longitudinal axis that is roughly aligned along an anterior/posterior axis of the disc 100. A given keel 144 also may have one or more holes or openings (not shown) that are perpendicular to the longitudinal axis of keel 114 to encourage bony in-growth, as described above with respect to superior endplate 110. Inferior endplate 140 may have an inferior surface (not shown) that is bi-convex, as described above with respect to superior surface 111, or may have another suitable configuration.

Figure 3:
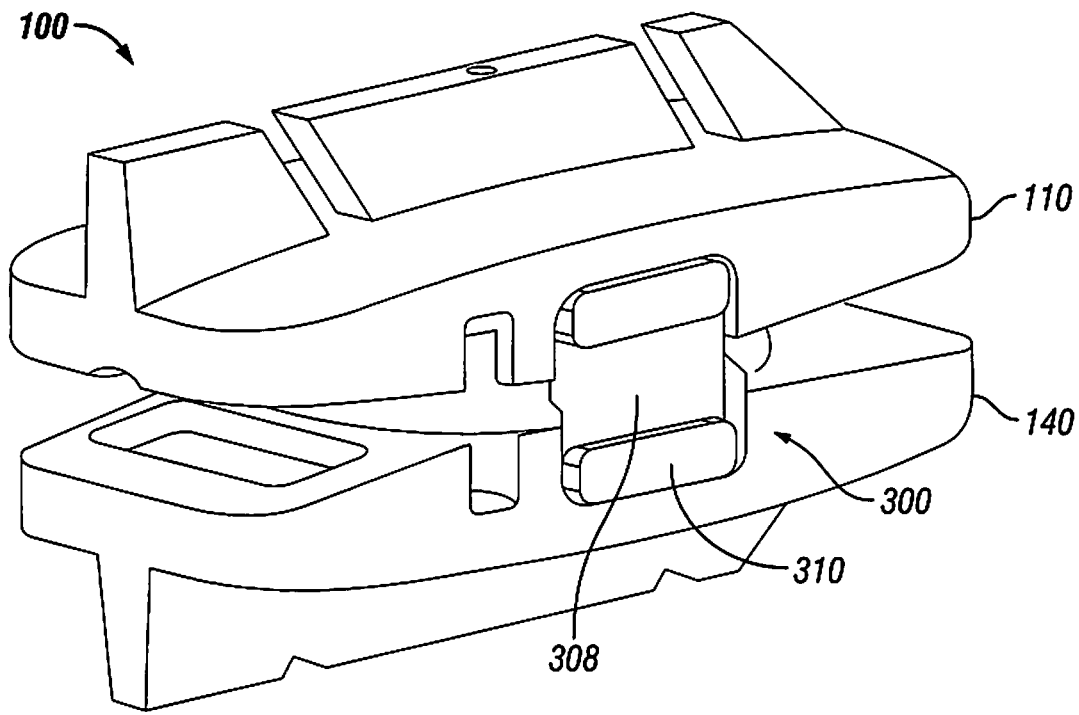
FIG. 3 is a side perspective view illustration of an artificial disc in accordance with an embodiment of the present disclosure.
Figure 4:
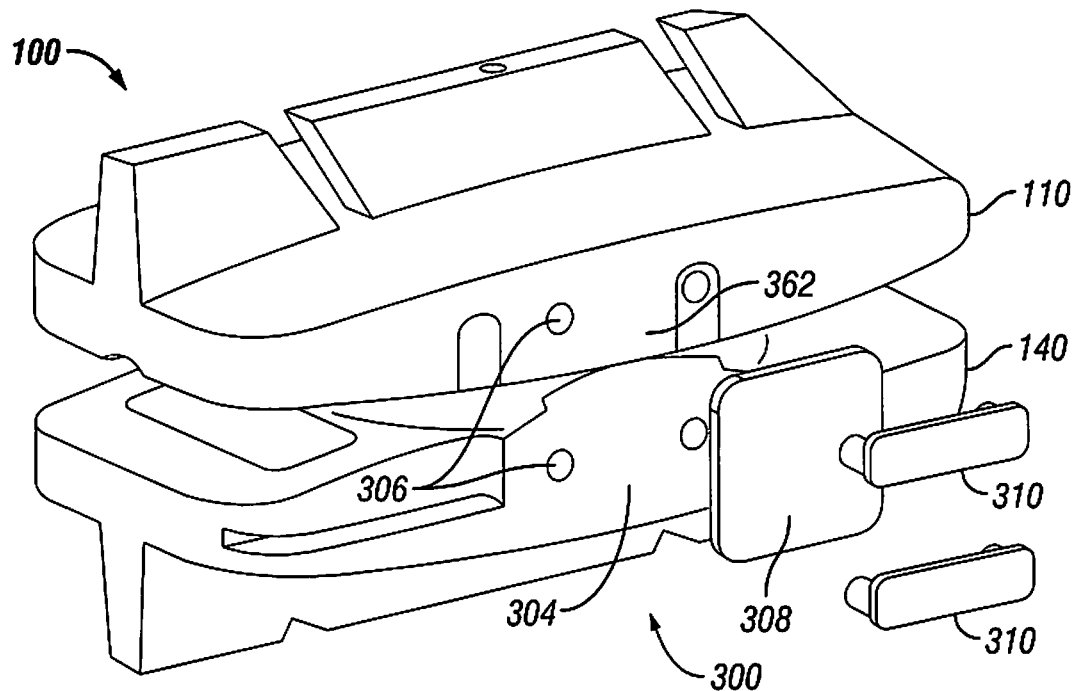
FIG. 4 is a partially-exploded side perspective view illustration of the artificial disc of FIG. 3.

Referring to FIGS. 3 and 4, an artificial disc 100 may include a support assembly 300. Support assembly 300 may include a first groove 302 (FIG. 4) disposed within a side surface of superior endplate 110, and a second groove 304 disposed within a side surface of inferior endplate 140. First and second grooves 302, 304 may be aligned and have similar configurations. Alternatively, first and second grooves 302 may have different configurations, if desired. In some embodiments, grooves may be on all four sides of artificial disc 100. In some embodiments, however, grooves may be only disposed on the two longer sides. First and second grooves 302, 304 may each include at least one lumen 306. In the embodiment shown, both first and second grooves 302, 304 each include two lumens 306 configured to receive a fastening member 310, such as, e.g., a staple or the like. When artificial disc 100 is fully assembled, grooves 302 and 304 may be configured to receive a sheath 308. That is, the combination of first and second grooves 302, 304 may have substantially the same geometry as sheath 308 when artificial disc 100 is in an assembled configuration. Lumens 306 may be configured to receive at least one fastening member 310. Sheath 308 may also include a plurality of lumens (not shown) that substantially correspond to the locations of lumens 306 disposed within first and second grooves 302, 304. Sheath 308 may be formed of a semi-flexible polyethylene terephthalate (PET) or another suitable material. Sheath 308 may additionally include an adhesive or other suitable securing mechanism to facilitate fixing the sheath to artificial disc 100. Fastening members 310 may be formed of any suitable biocompatible material. In some embodiments, support assembly 300 may limit the flexibility of artificial disc 100 and/or limit shear forces that may, e.g., separate components of artificial disc 100 from one another or otherwise disassemble artificial disc 100. In some embodiments, support assembly 300 may limit flexion, extension, and lateral bending of artificial disc 100.

Artificial disc 100 may include additional support assemblies 300 to further limit motion of components of artificial disc 100 with respect to one another. In one embodiment, artificial disc 100 may include two support assemblies 300 that are substantially parallel to one another. However, any other suitable number of support assemblies 300 may alternatively be utilized, if desired. Additional support assemblies 300 may be disposed along any side surface of superior endplate 110 and inferior endplate 140. Sheath 308 may alternatively include pegs for inserting through lumens 306, eliminating the need for fastening members 310. In another alternatively embodiment, lumens 306 may be eliminated and pegs may extend from first and second grooves 302, 304, or from a side surface of medical device 100 for inserting through holes disposed on sheath 308.

Figure 5:
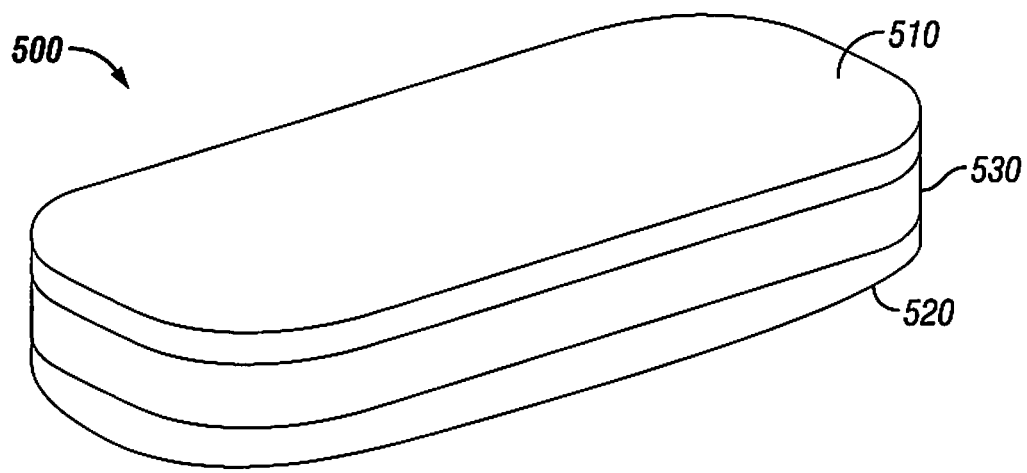
FIG. 5 is a side perspective view illustration of an artificial disc in accordance with an embodiment of the present disclosure.

An artificial disc 500 is depicted in FIG. 5 in accordance with an embodiment of the present disclosure. Artificial disc 500 may include a superior endplate 510, an inferior endplate 520, and a core 530 disposed between superior endplate 510 and inferior endplate 520. Core 530 may be fixedly secured to one or both of endplates 510 and 520. In some embodiments, all surfaces of artificial disc 500 may be atraumatic so as not to puncture through a disc annulus or other vertebral body. Superior endplate 510 and inferior endplate 520 may be formed from a rigid, bio-compatible material such as, e.g., titanium or polyetheretherketone (PEEK), among others. Core 530 may be formed of any suitable polymer, such as, e.g., silicone, PCU, or other suitable viscoelastic materials configured to provide compression and movement to core 530 to allow superior endplate 510 and inferior endplate 520 to articulate with respect to one another only by the natural elasticity of core 530. That is, in some embodiments, superior endplate 510 and inferior endplate 520 may each be flush with core 530. Each of superior endplate 510 and inferior endplate 520 may be biconvex, i.e., curved from left to right and front to back. In one embodiment, the exterior and/or bone-contacting surfaces of superior endplate 510 and inferior endplate 520 may be left smooth and/or untreated such that superior endplate 510 and inferior endplate 520 do not encourage bony on-growth in vivo, and are free to slide and/or articulate with respect to a given vertebral body. Thus, artificial disc 500 may be configured, in vivo, to have motion only at its center, e.g., at core 530, and at its exterior contact surfaces, e.g., the cephalad and caudal ends of artificial disc 500. In some embodiments superior endplate 510, inferior endplate 520, and core 530 may include varying cross-sections, radiopaque materials, and/or geometric features (e.g., to promote bony in-growth/on-growth). In some embodiments, a plasma spring (not shown) may be disposed on superior endplate 510 and/or inferior endplate 520. Artificial disc 500 may be inserted into a patient via a direct lateral procedure, although anterior or posterior procedures alternatively may be utilized. In an alternative embodiment, superior endplate 510 and inferior endplate 520 may be treated with a titanium and/or hydroxyapatite plasma spray coating to encourage bony on-growth, improving the strength and stability of the connection between the respective component and the underlying bone (e.g., a vertebral body). In some embodiments, artificial disc 500 may include therapeutic coatings, if desired.

Figure 6:
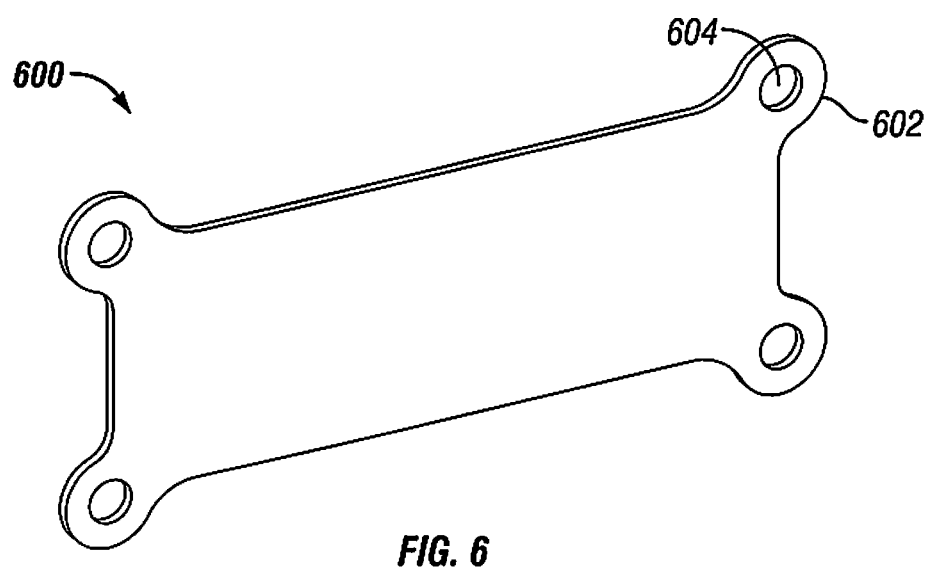
FIG. 6 is a front perspective view illustration of a cover plate in accordance with an embodiment of the present disclosure.

A cover plate 600 is depicted in FIG. 6 according to an embodiment of the present disclosure. Cover plate 600 may be formed from a shape memory material, such as, e.g., Nitinol or another suitable flexible or superelastic material. A plurality of features, e.g., protrusions, 602 may extend from an outer surface of cover plate 600. Each protrusion 602 may be atraumatic and have a varying cross-section. Each protrusion 602 may include an aperture 604 configured to facilitate suturing of cover plate 600 in vivo to a disc annulus or to a vertebral body. In the embodiment shown, cover plate 600 has four protrusions 602, though any other suitable number of protrusions alternatively may be utilized. In an alternative embodiment, a plurality of apertures 604 may be disposed within a surface of cover plate 600 having atraumatic, e.g., rounded corners, eliminating the need for any protrusions 602.

Figure 7:
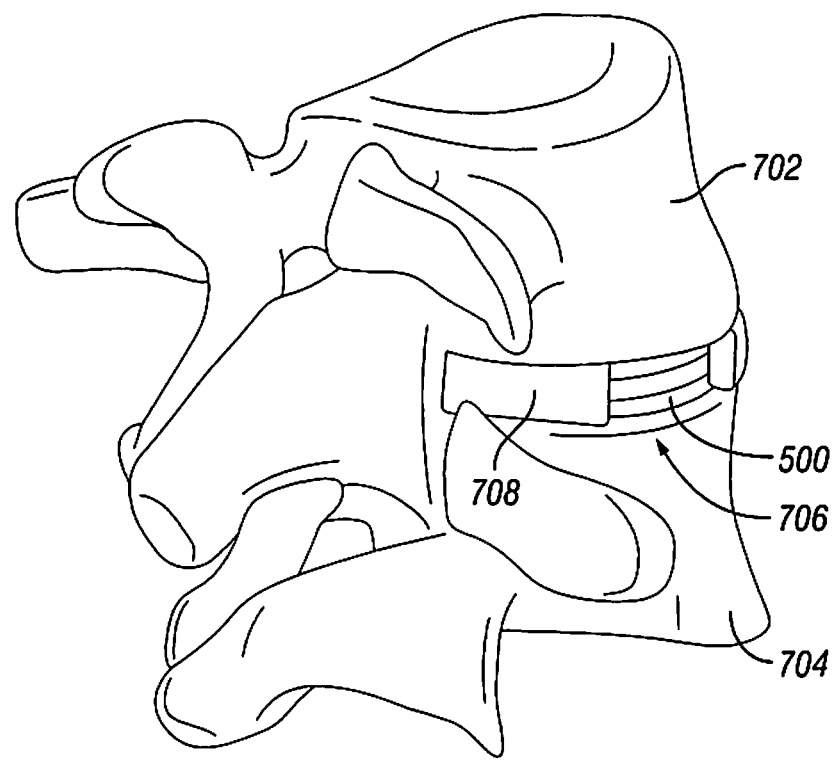
FIG. 7 is a perspective view illustration of the artificial disc of FIG. 5 in vivo and installed between vertebral bodies in accordance with an embodiment of the present disclosure.
Figure 8:
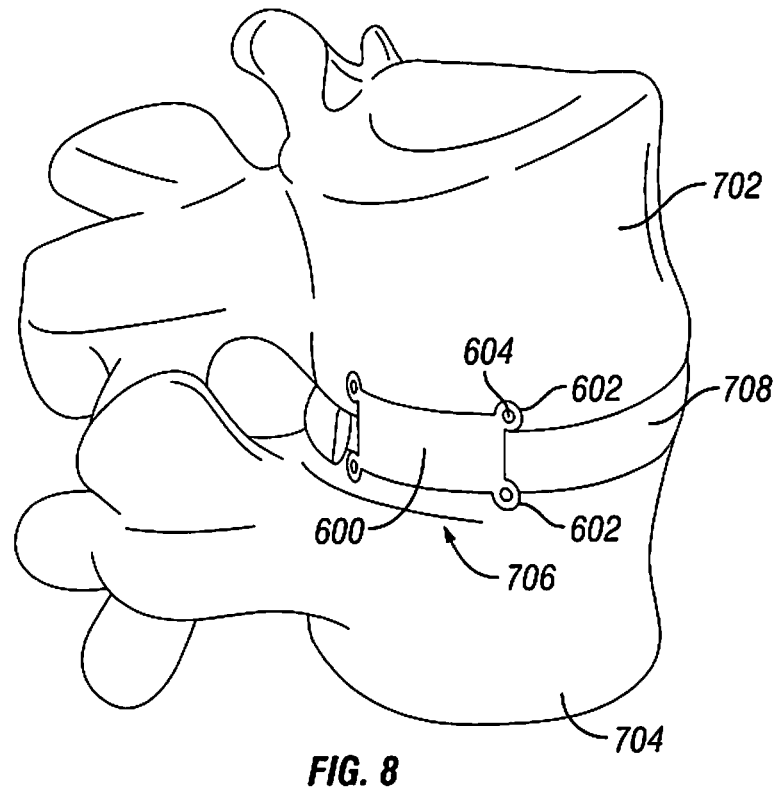
FIG. 8 is a perspective view illustration of the cover plate of FIG. 6 in vivo and installed adjacent vertebral bodies in accordance with an embodiment of the present disclosure.

In FIG. 7, a first vertebral body 702 and a second vertebral body 704 are shown during a disc replacement procedure. After a discectomy, material may have been removed from anterior ligaments and/or outer bands surrounding a damaged vertebral disc between first and second vertebral bodies 702, 704, forming an opening 706 in a disc annulus 708. Damaged material from the disc (e.g., a disc nucleus) may be removed, and an artificial disc 500 may be inserted between first and second vertebral bodies 702, 704 via a suitable procedure. As seen in FIG. 8, cover plate 600 may be utilized to cover the discectomy at opening 706 to keep artificial disc 500 secured between first and second vertebral bodies 702, 704. That is, cover plate 600 may keep artificial disc 500 from expulsing after the procedure is finalized. Cover plate 600 may be bent or folded to insert cover plate 600 through opening 706. In an assembled or installed configuration, cover plate 600 may be disposed within the outer circumference of first and second vertebral bodies 702, 704. When a compressive or bending force is released, and cover plate 600 is inserted through opening 706, cover plate 600 and/or protrusions 602 may urge toward an inner circumference of vertebral bodies 702, 704, preventing artificial disc from expulsing through opening 706. In some embodiments, at least one protrusion 602 may be secured against first vertebral body 702, while at least one other protrusion 602 may be secured against second vertebral body 704. In some embodiments, sutures may be placed through apertures 604 to additionally or alternatively secure cover plate 600 to first and second vertebral bodies 702, 704. In some embodiments, cover plate 600 may bias against artificial disc 500 to keep artificial disc 500 in place.

In some embodiments, artificial disc 500 may provide an implant having an elegant design having no parts that may cause wear debris. In some embodiments, the properties of viscoelastic core 530 may allow for dynamic motion at the implant level to absorb shock forces. Installation of artificial disc 500 may be relatively easy, repeatable, and have less blood loss as compared to the installation of other artificial discs. In some embodiments, cover plate 600 may secure artificial disc 500 for an extended period, such as, e.g., the entire remaining life of a patient. The shape and flexible properties of cover plate 600 may allow cover plate 600 to mimic the natural curvature of specific spinal geometries of a given patient. For example, cover plate 600 may mimic the natural curvature and specific geometries of first and second vertebral bodies 702, 704. In some embodiments, cover plate 600 may be used with other implants, or alternatively, in a procedure to repair a disc annulus 708, but not a disc nucleus or other damaged material, if desired.

Figure 9:
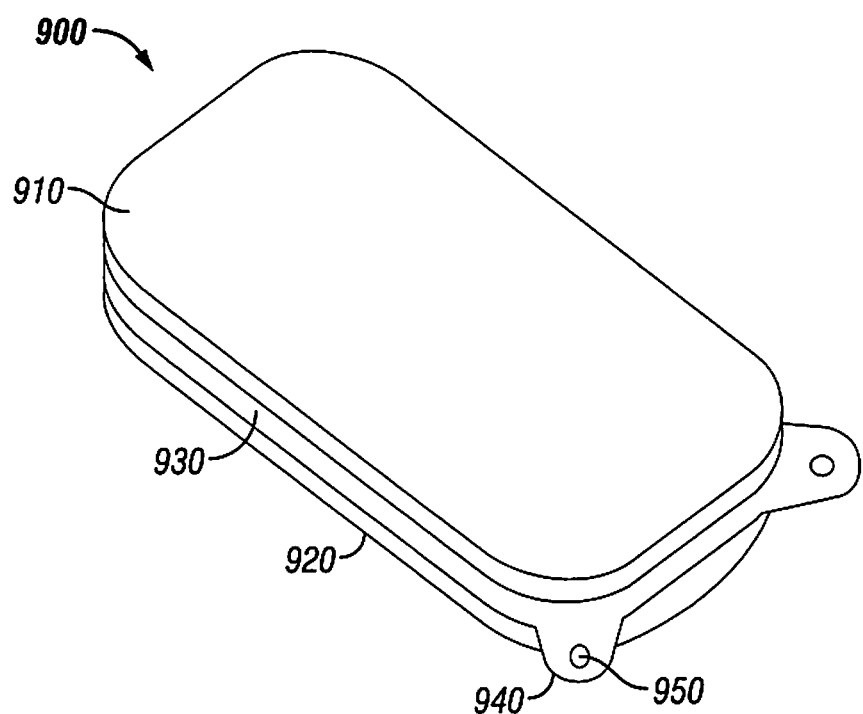
FIG. 9 is a side perspective view illustration of an artificial disc in accordance with another embodiment of the present disclosure.

An artificial disc 900 is depicted in FIG. 9 in accordance with another embodiment of the present disclosure. Artificial disc 900 may include a superior endplate 910, an inferior endplate 920, and a core 930 disposed between superior endplate 910 and inferior endplate 920. Superior endplate 910, inferior endplate 920, and core 930 may be substantially similar to superior endplate 510, inferior endplate 520, and core 530 described with reference to FIG. 5 except that core 930 may additionally include at least one securing mechanism 940 extending from an outer surface or core 930. Securing mechanism 940 may include at least one protrusion having an aperture 950, and may be formed from substantially the same material as core 930. In an alternative embodiment, securing mechanism may be made from a different material than core 930, or a combination of materials, if desired. Although depicted in two corners, securing mechanism 940 may be located at any position on the edge of artificial disc 900.

Figure 10:
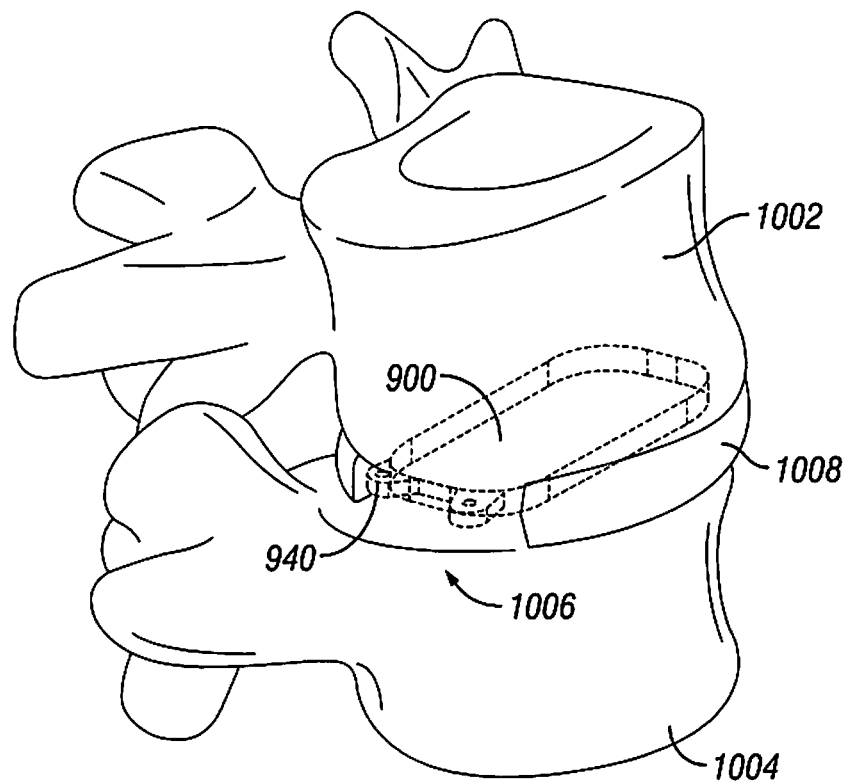
FIG. 10 is a perspective view illustration of the artificial disc of FIG. 9 in vivo and partially installed between vertebral bodies, while in a first configuration, in accordance with an embodiment of the present disclosure.
Figure 11:
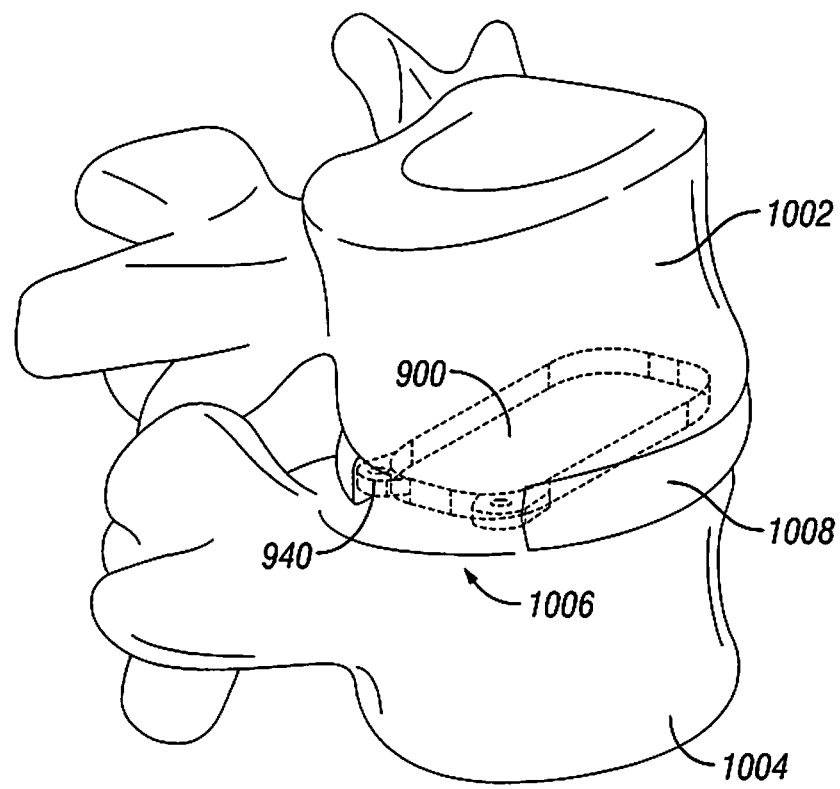
FIG. 11 is a perspective view illustration of the artificial disc of FIG. 9 in vivo and installed between vertebral bodies, while in a second configuration, in accordance with an embodiment of the present disclosure.

In FIG. 10, a first vertebral body 1002 and a second vertebral body 1004 are shown during a disc replacement procedure. After a discectomy, material may have been removed from anterior ligaments and/or outer bands surrounding a damaged vertebral disc between first and second vertebral bodies 1002, 1004, forming an opening 1006 in a disc annulus 1008. Damaged material, such as, e.g., a disc nucleus, may be removed from a vertebral disc, and an artificial disc 900 may be inserted between first and second vertebral bodies 1002, 1004. Protrusions 940 may be compressed and/or sutured together as shown in FIG. 8 to allow for insertion of artificial disc 900 between vertebral bodies 1002, 1004 through opening 1006. After insertion, the compressive force may be released or the suture may be severed, and protrusions 940 may then be moved (e.g., spring back) toward their initial resting position, and toward an inner circumference of disc annulus 1008 and/or first and second vertebral bodies 1002, 1004 as shown in FIG. 11.

In some embodiments, protrusions 940 may secure artificial disc 900 between first and second vertebral bodies 1002 and 1004 for an extended period, such as, e.g., the remaining lifetime of a patient. The shape and flexible properties of protrusions 940 may allow artificial device 900 to mimic the natural curvature of the spine of a given patient. Apertures 950 may further provide an additional mechanism for securing artificial disc 900.

Figure 12:
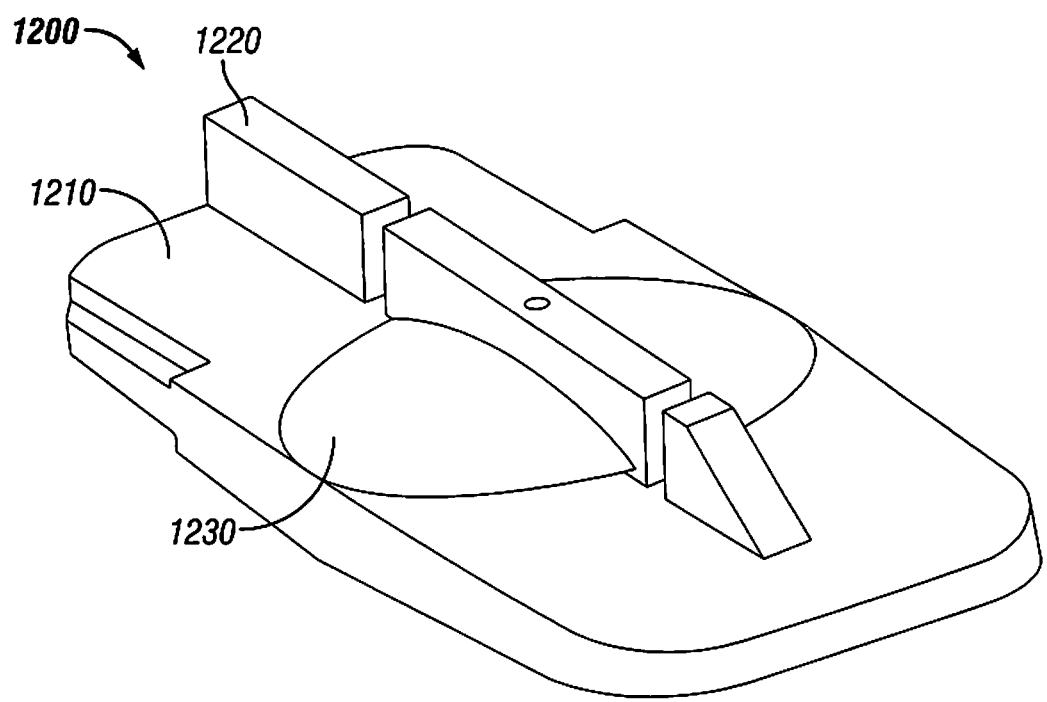
FIG. 12 is a perspective view illustration of an endplate in accordance with an embodiment of the present disclosure.

An exemplary endplate 1200 is depicted in FIG. 12. Endplate 1200 may be a superior or inferior endplate, if desired. Endplate 1200 may have an outer surface 1210. Surface 1210 may be bi-convex, i.e., curved from left to right and front to back, or have another suitable configuration. This curvature may give surface 1210 a partial dome or spherical shape. The curvature may be complementary to the natural curvature of an endplate of a vertebral body and may provide for an anatomical fit between surface 1210 and the vertebral body (not shown in FIG. 12). One or more serrated keels 1220 may be located on surface 1210. Each keel 1220 may have a longitudinal axis that is roughly aligned along an anterior/posterior axis of an artificial disc incorporating endplate 1200. Alternatively, endplate 1200 may have a smooth surface without any keels 1220. Endplate 1200 may further include a protrusion 1230 extending from bi-convex surface 1210 in a direction substantially perpendicular to the longitudinal axis of endplate 1200 (e.g., outward along the Y axis or vertical axis of the spine). Protrusion 1230 may be partially spherical or dome-shaped, although other shapes may be alternatively utilized, if desired. In some embodiments, keels 1220 may extend further outward along the Y axis from surface 1210 than protrusion 1230, though other suitable configurations may alternatively be utilized. Endplate 1200 may have a varying cross-section, if desired. Protrusion 1230 may be integral with surface 1210 or may be attached via a suitable mechanism. Further, protrusion 1230 may include geometrical features, such as e.g., dents, bumps, or the like. While depicted as extending along a first axis of endplate 1200, protrusion 1230 may alternatively extend a long a second axis of endplate 1200 that is substantially perpendicular to the first axis.

Figure 13:
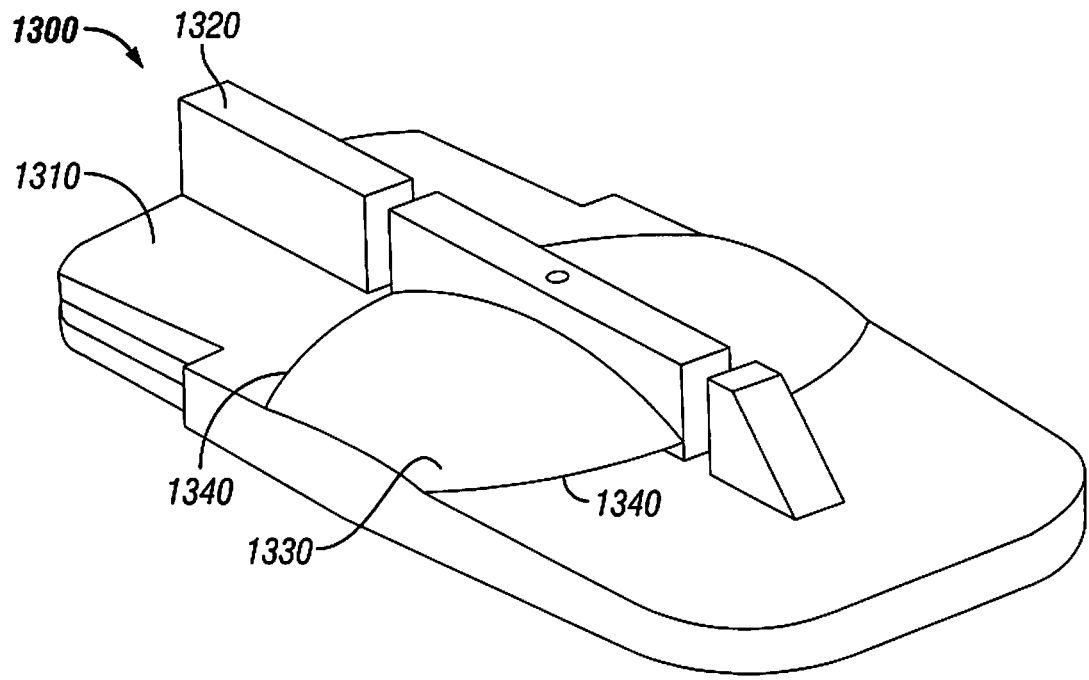
FIG. 13 is a perspective view illustration of an endplate in accordance with an embodiment of the present disclosure.

An exemplary endplate 1300 is depicted in FIG. 13 having an outer surface 1310 and one or more serrated keels 1320 that are substantially similar to outer surface 1210 and keels 1220 described with reference to FIG. 12. Alternatively, endplate 1300 may have a smooth surface without any keels 1320. Endplate 1300 may further include a protrusion 1330 extending from bi-convex surface 1310 in a direction substantially perpendicular to the longitudinal axis of endplate 1300 (e.g., outward along the Y axis or vertical axis of the spine). Protrusion 1330 may be generally partially barrel-shaped and have a variable radius, and may be defined by a pair of convex surfaces 1340 that are mirror-images of each other. However, other suitable shapes may alternatively be utilized, if desired. In some embodiments, keels 1320 may extend further outward along the Y axis from surface 1310 than protrusion 1330, though other suitable configurations may alternatively be utilized. Endplate 1300 may have a varying cross-section, if desired. Protrusion 1330 may be integral with surface 1310 or may be attached via a suitable mechanism. Further, protrusion 1330 may include geometrical features, such as e.g., dents, bumps, or the like. While depicted as extending along a first axis of endplate 1300, protrusion 1330 may alternatively extend a long a second axis of endplate 1300 that is substantially perpendicular to the first axis.

Figure 14:
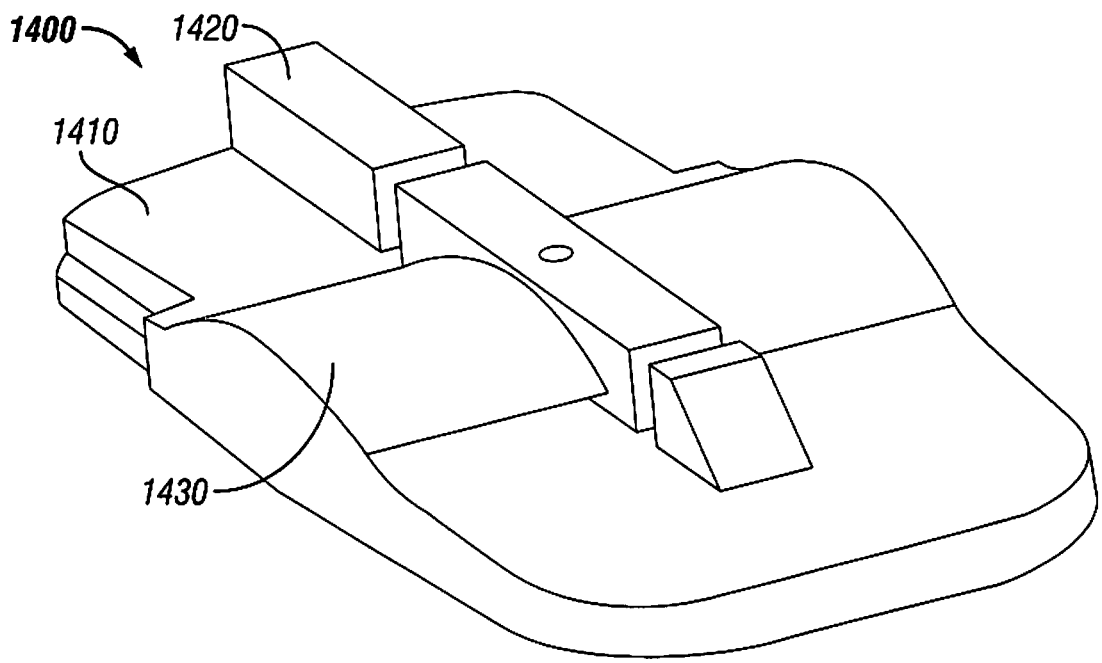
FIG. 14 is a perspective view illustration of an endplate in accordance with an embodiment of the present disclosure.

An exemplary endplate 1400 is depicted in FIG. 14 having an outer surface 1410 and one or more serrated keels 1420 that are substantially similar to outer surface 1210 and keels 1220 described with reference to FIG. 12. Alternatively, endplate 1400 may have a smooth surface without any keels 1420. Endplate 1400 may further include a protrusion 1430 extending from bi-convex surface 1410 in a direction substantially perpendicular to the longitudinal axis of endplate 1400 (e.g., outward along the Y axis or vertical axis of the spine). Protrusion 1430 may be generally partially cylindrical. However, other suitable shapes may alternatively be utilized, if desired. In some embodiments, keels 1420 may extend further outward along the Y axis from surface 1410 than protrusion 1430, though other suitable configurations may alternatively be utilized. Endplate 1400 may have a varying cross-section, if desired. Protrusion 1430 may be integral with surface 1310 or may be attached via a suitable mechanism. Further, protrusion 1430 may include geometrical features, such as e.g., dents, bumps, or the like. While depicted as extending along a first axis of endplate 1400, protrusion 1430 may alternatively extend a long a second axis of endplate 1400 that is substantially perpendicular to the first axis.

Protrusions 1230, 1330, and 1430 may facilitate insertion of artificial discs utilizing endplates 1200, 1300, and 1400, and may reduce impaction. Protrusions 1230, 1330, and 1430 may be disposed along superior and/or inferior endplates, and may provide load-bearing support in the most concave portions of the respective spinal vertebral endplates.

One consideration applicable to some embodiments of the present disclosure, may include the desire to maintain the same degree of rotations irrespective of disc position. This may be the case when the prosthetic/artificial disc is placed into the intervertebral space through a transforaminal approach. As the prosthetic disc is seated within the vertebral space at an angle offset from either the anterior-posterior axis of the vertebral bodies and/or the medial-lateral axis of the vertebral bodies, it may be desirable to provide uniform degrees of freedom between the articulating surfaces of the prosthetic disc to accommodate natural movement in the anterior-posterior direction and medial-lateral direction as well as provide for uniform degrees of freedom for coupled motion. This freedom of movement may be designed in conjunction with the shape of the prosthetic disc such that the shape of the disc, its stops, and other structural features do not limit the degrees of freedom in one particular direction more than in others.

Another consideration in some of the embodiments of the present disclosure contemplates the design of prosthetic discs in shapes that complement different implantation approaches. For example, prosthetic discs of a rectangular shape may be particularly well configured for insertion at an oblique angle. Because the transforaminal window is small, rectangular shaped prosthetic discs may provide a slim profile allowing easier insertion of the disc into the intervertebral space. Furthermore, these unique shapes may also provide sufficient disc surface area to form stable contacts with the bone of the intervertebral space. Additionally, certain sizes may provide improved stability of the disc itself by providing sufficient area for the articulating surface such that their respective movement is stable. Some or all of these factors may lead to disc designs with shape characteristics that make them particularly well suited for a transforaminal implantation, i.e., implantation at an oblique angle to the anterior-posterior or medial-lateral approaches. It has been found that prosthetic discs with a Length to Width ratio of about 2 to 1 are particularly well suited for transforaminal implantation in that said discs fit within the transforaminal window and provide optimum contact areas for bone contact and articulating surface area contacts. Thus for example, in one embodiment, the prosthetic disc may have a length of 30 mm and a width of 15 mm, although other suitable configurations are also contemplated. In alternative embodiments, the prosthetic disc may have lengths between about 26 and 34 mm and widths of between about 13 and 16 mm.

With respect to each embodiment herein described, the particular directions and configurations of the various surfaces can be modified and interchanged. Accordingly, the upper endplate may be the lower endplate and vice versa. Similarly, stops may be formed on either or both endplates. Additionally, keels may be on both or none of the endplates. Moreover, the prosthetic discs of the present disclosure may additionally contain any number of other features including for example, titanium sprays or other coatings or surface deposits that promote or help bony in-growth/on-growth. Similarly, the endplates themselves may be formed, in whole or in part, of materials or contain materials that promote bony in-growth/on-growth. Also, the various embodiments disclosed herein are not limited to construction out of any particular materials although metal on metal designs are one variety contemplated.

Any aspect set forth in any embodiment may be used with any other embodiment set forth herein. Every device and apparatus set forth herein may be used in a suitable medical procedure, such as, e.g., a vertebral disc replacement procedure, and may be advanced through any suitable body lumen and body cavity.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

We claim:

1. A method of installing an artificial disc within a patient, the artificial disc including a superior endplate having a bi-convex superior surface and a concave inferior surface, an inferior endplate having a bi-convex inferior surface, and a core assembly secured to the superior endplate and the inferior endplate, wherein the superior endplate and inferior endplate articulate with respect to each other only by the elasticity of the core assembly, the method including:

forming an opening in a vertebral disc annulus;

removing damaged vertebral disc material through the opening;

inserting the artificial disc between through the opening between a pair of adjacent vertebral bodies; and securing the artificial disc between the vertebral bodies wherein securing the artificial disc between the vertebral bodies includes securing a cover plate to at least one of the vertebral disc annulus and the inner circumference of one of the vertebral bodies to cover the opening.

2. The method of claim 1, wherein securing the artificial disc between the vertebral bodies further includes suturing the cover plate to at least one of the vertebral disc annulus and at least one of the pair of vertebral bodies.

3. The method of claim 1, wherein:

the core assembly includes at least one securing mechanism extending from an outer surface;

inserting the artificial disc further includes applying a compressive force to the securing mechanism; and securing the artificial disc between the vertebral bodies includes releasing the compressive force applied to the securing mechanism to allow the securing mechanism to secure against at least one of the vertebral disc annulus and the inner circumference of one of the vertebral bodies.

4. The method of claim 3, wherein securing the artificial disc between the vertebral bodies further includes suturing the securing mechanism to at least one of the vertebral disc annulus and at least one of the pair of vertebral bodies.

5. A method of installing an artificial disc within a patient, the artificial disc including a superior endplate having a bi-convex superior surface and a concave inferior surface, an inferior endplate having a bi-convex inferior surface, and a core assembly secured to the superior endplate and the inferior endplate, wherein the superior endplate and inferior endplate articulate with respect to each other only by the elasticity of the core assembly, the method including:

forming an opening in a vertebral disc annulus;

removing damaged vertebral disc material through the opening;

inserting the artificial disc between through the opening between a pair of adjacent vertebral bodies; and securing the artificial disc between the vertebral bodies, the core assembly includes at least one securing mechanism extending from an outer surface;

inserting the artificial disc further includes applying a compressive force to the securing mechanism; and securing the artificial disc between the vertebral bodies includes releasing the compressive force applied to the securing mechanism to allow the securing mechanism to secure against at least one of the vertebral disc annulus and the inner circumference of one of the vertebral bodies, wherein securing the artificial disc between the vertebral bodies further includes suturing the securing mechanism to at least one of the vertebral disc annulus and at least one of the pair of vertebral bodies.

* * * * *